US006235061B1

(12) United States Patent
Laurencin et al.

(10) Patent No.: US 6,235,061 B1
(45) Date of Patent: May 22, 2001

(54) POLY(ORGANOPHOSPHAZENE) MATRICES FOR BONE REPLACEMENT

(75) Inventors: Cato T. Laurencin, Somerville; Saadiq El-Amin, Brighton, both of MA (US); Archel M. A. Ambrosio, State College, PA (US); Shawn R. Pucher, San Diego, CA (US); Harry R. Allcock, State College, PA (US)

(73) Assignees: The Penn State Research Foundation, University Park, PA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 08/222,662

(22) Filed: Apr. 4, 1994

(51) Int. Cl.[7] ..................................................... A61F 2/28
(52) U.S. Cl. ................................. 623/23.57; 623/23.58; 623/23.75; 606/76; 523/115
(58) Field of Search ............................. 623/11, 16, 23.57, 623/23.58, 23.61, 23.75; 606/76; 523/113, 114, 115

(56) References Cited

U.S. PATENT DOCUMENTS

| | | |
|---|---|---|
| 3,893,980 | 7/1975 | Allcock et al. . |
| 4,440,921 | 4/1984 | Allcock et al. . |
| 4,495,174 * | 1/1985 | Allcock et al. ................... 424/78.37 |
| 4,543,379 | 9/1985 | Gettleman et al. . |
| 4,592,755 | 6/1986 | Penton et al. . |
| 4,880,622 * | 11/1989 | Allcock et al. ....................... 424/468 |
| 4,946,938 | 8/1990 | Magill et al. . |
| 4,975,280 * | 12/1990 | Schacht et al. ....................... 424/422 |
| 4,990,336 | 2/1991 | Silvestri et al. . |
| 5,104,947 | 4/1992 | Schacht et al. . |
| 5,306,305 * | 4/1994 | Lee ......................................... 623/16 |
| 5,380,329 * | 1/1995 | Elia et al. ............................... 606/72 |

OTHER PUBLICATIONS

Hawley's Condensed Chemical Dictionary, 11th Ed., (1987), p. 909.*
Allcock, H. R., "Synthesis of poly[(amino acid alkyl ester) phosphazenes]," *Macromolecules*, 10, 824–830 (1977).
Allcock, H. R., et al., "Hydrolysis pathways for aminophosphazanes," *Inorg. Chem.*, 21, 515–521 (1982).
Allcock, H. R., and T.J. Fuller, "Synthesis and Hydrolysis of Hexakis(imidazolyl)cyclotriphosphazene," *J. Am. Chem. Soc.*, 103, 2250–.
Allcock, H.R., et al., "Phosphonitrilic Compounds. XV. High Molecular Weight Poly[bix(amino)phosphazenes] and Mixed–Substituent Poly(aminophosphazenes)," *Inorg. Chem.* 11, (1972).
Allcock, H.R., et al., "Synthesis of Sugar–Substituted Cyclic and Polymeric Phosphazenes and Their Oxidation, Reduction, and Acetylation Reactions," *Macromolecules* 16, 715 (1983).

Allcock, H.R., et al., "Polyphosphazenes with Etheric Side Groups: Prospective Biomedical and Solid Electrolyte Polymers," *Macromolecules* 19, 1508 (1986).
Allcock, H.R., et al. "Amphiphilic polyphosphazenes as membrane materials: influence of side group on radiation cross–linking," *Biomaterials*, 19, 500 (1988).
Allcock, H.R., et al., "Glyceryl Polyphosphazenes: Synthesis, Properties, and Hydrolysis," *Macromolecules* 21, 1980 (1988).
Allcock, H.R., et al., "An Ionically Cross–Linkable Polyphosphazene: Poly[bis(carboxylatophenoxy)phosphazene] and Its Hydrogels and Membranes," *Macromolecu les* 22, 75 (1989).
Cima, Linda, et al. "Tissue engineering by cell transplantation using degradable polymer substrates," *J. Biomech., Eng.*, 113, 143–151 (1991).
Coombes, A.D.A. and J.D. Heckman, "Gel Casting of Resorbable Polymers: Processing and Applications," *Biomaterials*, 13(4), 217–224 (1992).
Eggli, P.S., et al., "Porous hydroxyapatite and tricalcium phosphate cylinders with two different pore size ranges implanted in the cancellous bone of rabbits", *Clin. Orthop.*, 232, 127–138 (1987).
Elgendy, H.M., et al. "Osteoblast–like cell (MC3T3–E1) proliferation on bioerodible polymers: An approach towards the development of a bone–bioerodible polymer composite material," *Biomaterials*, 14, 263–269 (1993).
Frame, J.W., "Hydroxyapatite as a biomaterial for alveolar ridge augmentation," *Int. J. Oral Maxillofacial Surgery*, 16, 642–55 (1987).
Friedlaender, G.E., "Current Concepts Review: Bone Grafts," *Journal of Bone and Joint Surgery*, 69A(5), 786–790 (1987).
Gilding, D.K., and A.M. Reed, "Biodegradable polymers for use in surgery: Polyglycolic acid/polylactic acid homo– and copolymers," *Polymer* 20, 1459–1464 (1979).
Grolleman, et al., *J. Controlled Release* 3, 143 (1986).
Hollinger, J.O., "Preliminary report on the osteogenic potential of a biodegradable copolymer of polyactide (PLA) and polyglycolide (PGA)." *J. Biomed. Mater. Res.* 17, 71–82 (1983).

(List continued on next page.)

*Primary Examiner*—Paul B. Prebilic
(74) *Attorney, Agent, or Firm*—Arnall Golden & Gregory, LLP

(57) ABSTRACT

A highly porous three-dimensional biodegradable poly(organophosphazene) matrix with hydrolytically unstable side chains is prepared and used as a scaffold for the growth of osteoblast cells. In a preferred embodiment, the poly(organophosphazene) includes between 10 and 90% hydrolytically unstable side chains including glucosyl, glyceryl, glyceryl, imidazolyl or ethoxy units, for example, poly[(methylphenoxy)(ethyl glycinato) phosphazene]. The addition of the glucosyl, glycinyl or glyceryl side chains to the polymer can also be used generally to enhance growth rates of cells adhered to the polymer, presumably through uptake and metabolism of the simple sugar or alcohol units.

8 Claims, No Drawings

OTHER PUBLICATIONS

Hollinger, J.O., and G.C. Battisone, "Biodegradable bone repair materials: Synthetic polymers and ceramics," *Clin. Orthop.*, 207, 290–305 (1986).

Jarcho, M. "Calcium Phosphate Ceramics as Hard Tissue Prosthetics," *Clinical Orthopedics and Related Research*, 157, 259–78 (1981).

Klatwitter, et al., "Application of porous ceramics for the attachment of load bearing orthopedic applications" *J. Biomed. Mater. Res. Symp.*, 2, 161 (1971).

Kulkarni, R.K., et al., "Biodegradable Poly(lactic acid) Polymers," *J. Biomedical Materials Research*, 5, 169–81 (1971).

Laurencin, Cato T., et al. "Use of polyphosphazenes for skeletal tissue regeneration," *J. Biom. Mater. Res.*, 27 (1993).

Laurencin, Cato T., et al., "Controlled release using a new bioerodible polyphosphazene matrix system," *J. Biomedical Mat. Res.*, 21 1231–1246 (1987).

Mikos, et al., "Prevascularization of biodegradable polymer scaffolds for hepatocyte transplantation", *Proc. ACS Div. of Polymer. Mater.*, 66, 33 (1992).

Ohgushi, H., et al., "Repair of bone defects with marrow cells and porous ceramics," *Acta Orthop. Scand.* 60 334–339 (1989).

Parsons, et al."Osteoconductive Composite Grouts for Orthopedic Use," *Annals N.Y. Academy of Sciences*, 523, 190–207 (1988).

Potin, P. and R. De Jaeger, "Polyphosphazenes: Synthesis, structures, properties, applications," *Eur. Polym. J.*, 27, 341–348 (1991).

Shimazaki, K. and V. Mooney, "Comparative study of porous hydroxyapatite and tricalcium phosphate as bone substitute," *J. Orthop. Res.* 3 301–310 (1985).

Vacanti, Charles A., et al, "Synthetic polymers seeded with chrondrocytes provide a template for new cartilage formation," *Plast. Reconstr. Surg.*, 88, 753–759 (1991).

van Blitterswijk, C.A., et al. "Macropore tissue ingrowth: a quantitative and qualitative study on hydroxyapatite ceramic," *Biomaterials* 7 137–143 (1986).

Wade, C.W.R., et al. "Biocompatibility of eight poly(organophosphazenes)," in *Organomet. Polym.*, C.E. Carraher, J.E. Sheats and C.U. Pitman, Jr., Eds., Academic Press, New York, 1978, pp. 283–288.

White and Shors, "Biomaterial aspects of Interpore 200 porous hydroxyapatite". *Dental Clinical of N. Amer.*, 30, 49–67 (1986).

\* cited by examiner

POLY(ORGANOPHOSPHAZENE) MATRICES FOR BONE REPLACEMENT

This invention was made with government support under Grant Number 9011170 awarded by the National Science Foundation. The government has certain rights in the invention.

BACKGROUND OF THE INVENTION

The present invention is generally in the area of synthetic materials for bone repair and replacement, and is particularly a poly(organophosphazene) three dimensional matrix.

Successful design of an implant to replace skeletal tissue requires knowledge of the structure and mechanical properties of bone and an understanding of the means by which grafts become incorporated into the body. This information can then be used to define desirable characteristics of the implant to ensure that the graft functions in a manner comparable to organic tissue.

A graft may be necessary when bone fails and does not repair itself in the normal amount of time or when bone loss occurs through fracture or tumor. Bone grafts must serve a dual function: to provide mechanical stability and to be a source of osteogenesis. Since skeletal injuries are repaired by the regeneration of bone rather than by the formation of scar tissue, grafting is a viable means of promoting healing of osseous defects, as reviewed by Friedlaender, G. E., "Current Concepts Review: Bone Grafts," *Journal of Bone and Joint Surgery*, 69A(5), 786–790 (1987). Osteoinduction and osteoconduction are two mechanisms by which a graft may stimulate the growth of new bone. In the former case, inductive signals of little-understood nature lead to the phenotypic conversion of connective tissue cells to bone cells. In the latter, the implant provides a scaffold for bony ingrowth.

The bone remodeling cycle is a continuous event involving the resorption of pre-existing bone by osteoclasts and the formation of new bone by the work of osteoblasts. Normally, these two phases are synchronous and bone mass remains constant. However, the processes become uncoupled when bone defects heal and grafts are incorporated. Osteoclasts resorb the graft, a process which may take months. More porous grafts revascularize more quickly and graft resorption is more complete. After the graft has been resorbed, bone formation begins. Bone mass and mechanical strength return to near normal.

Present methods for the repair of bony defects include grafts of organic and synthetic construction. Three types of organic grafts are commonly used: autografts, allografts, and xenografts. An autograft is tissue transplanted from one site to another in the patient. The benefits of using the patient's tissue are that the graft will not evoke a strong immune response and that the material is vascularized, which allows for speedy incorporation. However, using an autograft requires a second surgery, which increases the risk of infection and introduces additional weakness at the harvest site. Further, bone available for grafting may be removed from a limited number of sites, for example, the fibula, ribs and iliac crest. An allograft is tissue taken from a different organism of the same species, and a xenograft from an organism of a different species. The latter types of tissue are readily available in larger quantities than autografts, but genetic differences between the donor and recipient may lead to rejection of the graft.

Synthetic implants may obviate many of the problems associated with organic grafts. Further, synthetics can be produced in a variety of stock shapes and sizes, enabling the surgeon to select implants as his needs dictate, as described by Coombes, A. D. A. and J. D. Heckman, "Gel Casting of Resorbable Polymers: Processing and Applications," *Biomaterials*, 13(4), 217–224 (1992). Metals, calcium phosphate ceramics and polymers have all been used in grafting applications.

Calcium phosphate ceramics are used as implants in the repair of bone defects because these materials are non-toxic, non-immunogenic, and are composed of calcium and phosphate ions, the main constituents of bone (Jarcho, 1981; Frame, J. W., "Hydroxyapatite as a biomaterial for alveolar ridge augmentation," *Int. J. Oral Maxillofacial Surgery*, 16, 642–55 (1987); Parsons, et al. "Osteoconductive Composite Grouts for Orthopedic Use," *Annals N.Y. Academy of Sciences*, 523, 190–207 (1988)). Both tricalcium phosphate (TCP) [$Ca_3(PO_4)2$] and hydroxyapatite (HA) [$Ca_{10}(PO_4)_6(OH_2)$] have been widely used. However, the mechanical properties of calcium phosphate ceramics make them ill-suited to serve as a structural element. Ceramics are brittle and have low resistance to impact loading.

Over the last decade there has been a tremendous increase in applications for polymeric materials. They have been used widely for surgical implants, and artificial organs, as reviewed by D. K. Gilding and A. M. Reed, "Biodegradable polymers for use in surgery: Polyglycolic acid/polylactic acid homo-and copolymers," *Polymer* 20, 1459–1464 (1979); J. O. Hollinger and G. C. Battisone, "Biodegradable bone repair materials: Synthetic polymers and ceramics," *Clin. Orthop.*, 207, 290–305 (1986); L. Cima, et al. "Tissue engineering by cell transplantation using degradable polymer substrates," *J. Biomech., Eng.*, 113, 143–151 (1991); C. A. Vacanti, et al. "Synthetic polymers seeded with chrondrocytes provide a template for new cartilage formation," *Plast. Reconstr. Surg.*, 88, 753–759 (1991); J. O. Hollinger, "Preliminary report on the osteogenic potential of a biodegradable copolymer of polylactide (PLA) and polyglycolide (PGA)." *J. Biomed. Mater. Res.* 17, 71–82 (1983); and P. Potin and R. De Jaeger, "Polyphosphazenes: Synthesis, structures, properties, applications," *Eur. Polym. J.*, 27, 341–348 (1991). These materials are well suited to implantation as they can serve as a temporary scaffold to be replaced by host tissue, degrade by hydrolysis to non-toxic products, and be excreted, as described by Kulkarni, et al., *J. Biomedical Materials Research*, 5, 169–81 (1971); Hollinger, J. O. and G. C. Battistone, "Biodegradable Bone Repair Materials," *Clinical Orthopedics and Related Research*, 207, 290–305 (1986). Four polymers widely used in medical applications are poly(paradioxanone) (PDS), poly(lactic acid) (PLA), poly(glycolic acid) (PGA), and PLAGA copolymers. Copolymerization enables modulation of the degradation time of the material. By changing the ratios of crystalline to amorphous polymers during polymerization, properties of the resulting material can be altered to suit the needs of the application.

These polymers, including poly(lactide-co-glycolic) acid (PLAGA), have been used as polymer composites for bone replacement as reported by H. M. Elgendy, et al. "Osteoblast-like cell (MC3T3-E1) proliferation on bioerodible polymers: An approach towards the development of a bone-bioerodible polymer composite material," *Biomaterials*, 14, 263–269 (1993). Substituted polyphosphazenes have been shown to support osteogenic cell growth, as reported by C. T. Laurencin, et al. "Use of polyphosphazenes for skeletal tissue regeneration," *J. Biom. Mater. Res.*, 27 (1993). Coombes and Heckman 1992 and Hollinger 1983 have attempted to create poly(lactide-co-glycolide)

[(C₃H₄O₂)ₓ(C₂H₂O₂)ᵧ] implants as bone substitute. Although initial results by Hollinger suggested that polymer may aid in osteoinduction in the early bone repair process, by 42 days, the rate of repair was equivalent in controls and experimental defect sites. As reported by Coombes and Heckman, after eight weeks degradation in phosphate buffered saline (PBS), the strength of the material had deteriorated significantly. Moreover, the microporous structure (pores 205 μm in diameter) has been shown to be too small to permit the ingrowth of cells, as reported by Friedlander, G. E. and V. M. Goldberg, Bone and Cartilage Allografts, Park Ridge: *American Academy of Orthopedic Surgeons*, 1991; Jarcho, M. "Calcium Phosphate Ceramics as Hard Tissue Prosthetics," *Clinical Orthopedics and Related Research*, 157, 259–78 (1981). Accordingly, from a mechanical as well as a biological standpoint, this matrix is not ideal for use as a substitute bone graft material.

Poly(organophosphazenes) are high molecular weight polymers containing a backbone of alternating phosphorus and nitrogen atoms. There are a wide variety of polyphosphazenes, each derived from the same precursor polymer, poly(dichlorophosphazene). The chlorine-substituted species can be modified by replacement of the chlorine atoms by different organic nucleophiles such as o-methylphenoxide along with amino acids. The physical and chemical properties of the polymer can be altered by adding various ratios of hydrolytic sensitive side chains such as ethyl glycinate, as described by C. W. R. Wade, et al. "Biocompatibility of eight poly(organophosphazenes)," in *Organomet. Polym.*, C. E. Carraher, J. E. Sheats and C. U. Pitman, Jr., Eds., Academic Press, New York, 1978, pp. 283–288; and H. R. Allcock and T. J. Fuller, "Synthesis and Hydrolysis of Hexakis(imidazolyl)cyclotriphosphazene," *J. Am. Chem. Soc.*, 103, 2250–2256 (1981). This will affect the degradation of the polymer as an implantable and biodegradable material as well as vary the support of osteogenic cells for bone and tissue implants, as shown by Laruencin, et al. (1993). However, even with knowledge of degradation properties of the polymer, as in the case of PLGA, it is still necessary to develope a three dimensional matrix system in order to maximize growth, increase cell attachment and promote permanent fixation by ingrowth of living tissue which has desireable properties in vivo.

It is therefore an object of the present invention to provide a three dimensional matrix for regeneration of skeletal tissues which is biocompatible and biodegradable, and methods for preparation thereof.

It is a further object of the present invention to provide methods to manipulate cell growth on synthetic biocompatible, biodegradable polymeric matrices.

SUMMARY OF THE INVENTION

A highly porous three-dimensional biodegradable poly(organophosphazene) matrix with hydrolytically unstable side chains is prepared and used as a scaffold for the growth of osteoblast cells. In a preferred embodiment, the polyphosphazene includes between 10 and 90% hydrolytically unstable side chains including glucosyl, glycinyl, glyceryl, imidazolyl or ethoxy units, for example, poly[(methylphenoxy)(ethyl glycinato)phosphazene]. The addition of the glucosyl or glycinyl side chains to the polymer can also be used generally to enhance growth rates of cells adhered to the polymer, presumably through uptake and metabolism of the simple sugar or alcohol units.

As demonstrated by the examples, poly(organophosphazene)polymer substituted with 40% methylphenoxy and 60% ethyl glycinato side chains was fabricated into a porous three-dimensional matrix with an average pore density of 165 μm using a salt removal technique. Characterization by environmental scanning electron microscopy (ESEM) revealed an interconnecting porous network throughout the matrix with an even distribution of pores over the entire surface of the matrix. Osteoblast-like cells (MC3T3-E1) adhered to and grown on two-dimensional non-porous matrices and three-dimensional porous poly(organophosphazene) surfaces showed similar growth characteristics up to seven days. However, the growth and adhesion of the cells markedly increased on the three-dimensional matrices up to 21 days in culture, in contrast to the number of cells on the two-dimensional matrices which continued to decline. Characterization by light microscopy revealed cells growing within the pores as well as the surface of the matrix as early as the first day after seeding.

DETAILED DESCRIPTION OF THE INVENTION

A porous three-dimensional biodegradable biocompatible poly(organophosphazene) matrix system has been developed which is useful in the regeneration of skeletal tissue and bone.

Synthesis and Selection of Polymers

Poly(organophosphazenes) are polymers with backbones consisting of alternating phosphorus and nitrogen, separated by alternating single and double bonds. Each phosphorous atom is covalently bonded to two pendant groups ("R"). The repeat unit in poly(organophosphazenes) has the following general formula:

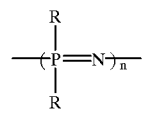

wherein n is an integer.

The substituent ("R") can be any of a wide variety of moieties that can vary within the polymer, including but not limited to aliphatic, aryl, aralkyl, alkaryl, carboxylic acid, heteroaromatic, carbohydrates, including glucose, heteroalkyl, halogen, (aliphatic)amino- including alkylamino-, heteroaralkyl, di(aliphatic)amino- including dialkylamino-, arylamino-, diarylamino-, alkylarylamino-, -oxyaryl including but not limited to -oxyphenylCo₂H, -oxyphenylSo₃H, -oxyphenylhydroxyl and -oxyphenylPO₃H; -oxyaliphatic including -oxyalkyl, -oxy(aliphatic)CO₂H, -oxy(aliphatic)SO₃H, -oxy(aliphatic)PO₃H, and -oxy(aliphatic)hydroxyl, including -oxy(alkyl)hydroxyl; -oxyalkaryl, -oxyaralkyl, -thioaryl, -thioaliphatic including -thioalkyl, -thioalkaryl, -thioaralkyl, —NHC(O)O-(aryl or aliphatic), —O—[(CH₂)ₓO])ᵧ—CH₂)ₓNH₂, —O—[(CH₂)ₓO]ᵧCH₂)ₓNH(CH2)ₓSO₃H, and —O—[(CH₂)ₓO]ᵧ-(aryl or aliphatic), wherein x is 1–8 and y is an integer of 1 to 20. The groups can be bonded to the phosphorous atom through, for example, an oxygen, sulfur, nitrogen, or carbon atom. The polymers can be designed to be hydrophobic, amphiphilic, or hydrophilic; water-stable or water-erodible; crystalline or amorphous; or bioinert or bioactive. As used herein, the polymers should be bioerodible over a period of between one and three months in vivo.

The term amino acid, as used herein, refers to both natural and synthetic amino acids, and includes, but is not limited to, alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

The term amino acid ester refers to the aliphatic, aryl or heteroaromatic carboxylic acid ester of a natural or synthetic amino acid.

The term alkyl, as used herein, refers to a saturated straight, branched, or cyclic hydrocarbon, or a combination thereof, typically of $C_1$ to $C_{20}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, and decyl.

The term (alkyl or dialkyl)amino refers to an amino group that has one or two alkyl substituents, respectively.

The terms alkenyl and alkynyl, as used herein, refers to a $C_2$ to $C_{20}$ straight or branched hydrocarbon with at least one double or triple bond, respectively.

The term aryl, as used herein, refers to phenyl or substituted phenyl, wherein the substituent is halo, alkyl, alkoxy, alkylthio, haloalkyl, hydroxyalkyl, alkoxyalkyl, methylenedioxy, cyano, C(O) (lower alkyl), —$CO_2H$, —$SO_3H$, —$PO_3H$, —$CO_2$alkyl, amide, amino, alkylamino and dialkylamino, and wherein the aryl group can have up to 3 substituents.

The term aliphatic refers to hydrocarbon, typically of $C_1$ to $C_{20}$, that can contain one or a combination of alkyl, alkenyl, or alkynyl moieties, and which can be straight, branched, or cyclic, or a combination thereof.

The term halo, as used herein, includes fluoro, chloro, bromo, and iodo.

The term aralkyl refers to an aryl group with an alkyl substituent.

The term alkaryl refers to an alkyl group that has an aryl substituent, including benzyl, substituted benzyl, phenethyl or substituted phenethyl, wherein the substituents are as defined above for aryl groups.

The term heteroaryl or heteroaromatic, as used herein, refers to an aromatic moiety that includes at least one sulfur, oxygen, or nitrogen in the aromatic ring, and that can be optionally substituted as described above for aryl groups. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbozolyl, oxazolyl, thiazolyl, isothiazolyl, 1,2,4-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl.

The term heteroalkyl, as used herein, refers to an alkyl group that includes a heteroatom such as oxygen, sulfur, or nitrogen (with valence completed by hydrogen or oxygen) in the carbon chain or terminating the carbon chain.

In one embodiment, the poly(organophosphazene) contains (i) ionized or ionizable pendant groups, and (ii) pendant groups that are susceptible to hydrolysis under the conditions of use, to impart biodegradability to the polymer. Suitable hydrolyzable groups include, for example, chlorine, amino acid, amino acid ester, imidazolyl, glycinyl, glyceryl, glucosyl, and ethoxy, most preferably not ethoxy or chlorine.

The degree of hydrolytic degradability of the polymer will be a function of the percentage of pendant groups susceptible to hydrolysis and the rate of hydrolysis of the hydrolyzable groups. The hydrolyzable groups are believed to be replaced by hydroxyl groups in aqueous environments to provide P-OH bonds that impart hydrolytic instability to the polymer.

While the acidic or basic groups are usually on nonhydrolyzable pendant groups, they can alternatively, or in combination, also be positioned on hydrolyzable groups.

For the embodiment described herein, the side groups (the R groups in formula 1) consist of between 10 and 90% glycosyl, glycinyl, or glyceryl units, or between 10 to 90%, more preferably 10 to 30%, ethoxy or imidazolyl units. Typically, the remaining side groups will be non-biodegradable side chains.

Specific examples of hydrolyzable side chains are unsubstituted and substituted imidazoles and amino acid esters in which the group is bonded to the phosphorous atom through an amino linkage. Poly(organophosphazenes) in which both R groups are attached in this manner are known as poly (aminophosphazenes).

In imidazolyl-substituted poly(organophosphazenes), some of the "R" groups on the poly(organophosphazene) backbone are imidazole rings, attached to phosphorous in the backbone through a ring nitrogen atom. Other "R" groups can be organic residues that do not participate in hydrolysis, such as methyl phenoxy groups or other groups shown in Allcock, at al., *Macromolecule* 10, 824–830 (1977), hereby incorporated by reference.

Specific examples of R groups that are not capable of hydrolysis are alkyl, aralkyl, or aryl group having 20 carbon atoms or less (more preferably 12 carbon atoms or less); or a heteroalkyl or heteroaryl group having 20 or less carbons and heteroatoms (more preferably 12 or less carbon or heteroatoms). If the alkyl chain is too long, the polymer will be totally insoluble in water. The groups can be bonded to the phosphorous atom through e.g., an oxygen, sulfur, nitrogen, or carbon atom.

In general, when the poly(organophosphazene) has more than one type of pendant group, the groups will vary randomly throughout the polymer, and the polyphosphazene is thus a random copolymer. Phosphorous can be bound to two like groups, or two different groups. Polyphosphazenes with two or more types of pendant groups can be produced by reacting poly(dichlorophosphazene) with the desired nucleophile or nucleophiles in a desired ratio. The resulting ratio of pendant groups in the polyphosphazene will be determined by a number of factors, including the ratio of starting materials used to produce the polymer, the temperature at which the nucleophilic substitution reaction is carried out, and the solvent system used. While it is very difficult to determine the exact substitution pattern of the groups in the resulting polymer, the ratio of groups in the polymer can be easily determined by one skilled in the art.

Poly(organophosphazenes) can be made by displacing the chlorines in poly(dichlorophosphazene) with a selected substituent group or groups. Desired proportions of hydrolyzable to nonhydrolyzable side chains in the polymer can be achieved by adjusting the quantity of the corresponding nucleophiles that are reacted with poly (dichlorophosphazene). The preferred polyphosphazenes have a molecular weight of over 1,000.

Methods for synthesis of poly(organophosphazenes) are described by Allcock, H. R.; et al., *Inorg. Chem.* 11, 2584 (1972); Allcock, et al., *Macromolecules* 16, 715 (1983); Allcock, et al., *Macromolecules* 19, 1508 (1986); Allcock, H. R.; Gebura, M.; Kwon, S.; Neenan, T. X. *Biomaterials*, 19, 500 (1988); Allcock, et al., *Macromolecules* 21, 1980 (1988); Allcock, et al., *Inorg. Chem.* 21(2), 515–521 (1982);

Allcock, et al., *Macromolecules* 22, 75 (1989); U.S. Pat. Nos. 4,440,921, 4,495,174 and 4,880,622 to Allcock, et al.; U.S. Pat. No. 4,946,938 to Magill, et al., and Grolleman, et al., *J. Controlled Release* 3, 143 (1986), the teachings of which are specifically incorporated herein. Other patents on poly(organophsphazenes) include U.S. Pat. Nos. 4,440,921, 4,880,622, 3,893,980, 4,990,336, 4,975,280, 5,104,947, and 4,592,755.

In the preferred embodiment described in the following detailed examples, a matrix is formed from poly[(p-methylphenoxy)(ethyl glycinato)phosphazene].

Method of Manufacture

A particulate leaching process is used to create a porous polymeric matrix. Generally, particles are suspended in a polymer solution, the polymer solvent is removed, and the particles are leached out of the hardened polymer.

Polymer solvents.

The polymer is dissolved in a solvent that does not adversely affect the polymer or the particle to be suspended in the polymer solution, most preferably a volatile organic solvent. The relative amount of solvent will have a minimal effect on the structure of the produced matrix, but will affect the solvent evaporation time. A solution of polymer is made in an organic solvent such as tetrahydrofuran (THF) or mixtures of THF or other etheric solvents such as glyme, diglyme, or chloroform. The concentration of polymer in solvent will typically be in the range of between one and fifty percent, preferably between 10 and 30% w/v.

Particle dispersion in polymer

The particles can be any salt that forms crystals or particles having a diameter of approximately 100 to 250 microns, which is easily removed from and does not react with the polymer, and is non-toxic if some residue remains in the polymer after leaching. Examples other than salts include proteins such as gelatin and agarose, starches, polysaccharides such as alginate and other polymers. Preferably, the salt is a sodium salt, such as sodium chloride, sodium tartrate and sodium citrate, and other water soluble salts or compounds not soluble in the polymer solvent, for example, THF. The most preferred salt is sodium chloride.

Preferably, the particles are first sieved through a mesh or a series of screens to provide particles of relatively uniform diameter. The particles are added to a polymer solution as described below in the examples. The initial salt weight fraction is preferably between 0.5 and 0.9 dry weight percent. The corresponding initial polymer dry weight fraction is therefore between 0.1 and 0.5 weight percent. The initial salt weight fraction is instrumental in determining the characteristics of the polymer matrix.

Shaping of the Matrix.

The polymer solution can be cast into any appropriate mold, with the dried polymeric matrix retaining the shape of the mold. The solvent is evaporated from the salt and polymer mixture over a period of time, for example, 24 hours at room temperature. Any residual solvent is subsequently removed by lyophilization. The resulting mixture will be in the form of a polymer matrix interspersed with particles.

Particle leaching

The resulting polymer and particle composite matrix is immersed in a liquid in which the particle is soluble for a sufficient amount of time to allow leaching of substantially all of the particles, but which does not dissolve or detrimentally alter the polymer. The preferred liquid is water, most preferably distilled-deionized water, which does not dissolve the polymer nor cause measurable hydrolysis of the polymer within the time required for processing. Preferably, the particle is leached out of the matrix in a vessel containing distilled-deionized water for a period of 48 hours. The vessel can be placed in a heated waterbath or incubator and shaken to enhance particle leaching. Most preferably, the vessel of water is placed in a waterbath heated to approximately 37° C. and is shaken at approximately 100 rpm to enhance the leaching process.

Removal of the particles will create a polymer matrix having a plurality of relatively evenly spaced interconnected interstitial spaces or pores, formerly occupied by the particle crystals, into which cells can migrate, attach, and proliferate. The porosity of the matrix is very high, typically between 60 and 90%.

The polymer matrix is dried for a sufficient amount of time to remove any water that may be occupying the pores. Preferably, the polymer matrix is air-dried for approximately 12 hours followed by vacuum-drying with a lyophilizer for approximately 24 hours.

Porosity

An important feature of the matrix system is that it is porous. A porous system allows an interconnecting pore network, as described by H. R. Allcock, et al., "Synthesis of poly[(amino acid alkyl ester)phosphazenes]," *Macromolecules*, 10, 824–830 (1977); H. R. Allcock, et al., "Hydrolysis pathways for aminophosphazenes," *Inorg. Chem.*, 21, 515–521 (1982); Mikos, et al., "Prevascularization of biodegradable polymer scaffolds for hepatocyte transplantation", *Proc. ACS Div. of Polymer. Mater.*, 66, 33 (1992); and Eggli, P. S., et al., "Porous hydroxyapatite and tricalcium phosphate cylinders with two different pore size ranges implanted in the cancellous bone of rabbits", *Clin. Orthop.*, 232, 127–138 (1987); which facilitates the invasion of cells and promotes an organized growth of the incoming cells and tissue. The porosity has been demonstrated to influence the biocompatibility and bony integration on various porous materials by White. and Shors, "Biomaterial aspects of Interpore 200 porous hydroxyapatite". *Dental Clinical of N. Amer.*, 30, 49–67 (1986). Klaitwatter, et al., "Application of porous ceramics for the attachment of load bearing orthopedic applications" *J. Biomed. Mater. Res. Symp.*, 2, 161 (1971), have shown that a pore size of over a 100 $\mu$m suitable and necessary for regeneration of cells and bony ingrowth.

As described above, the matrix resulting from the leaching process has a pore size in the range of between approximately 100 and 250 microns. This is achieved by selection of the size of the leachable particles.

Implantation of the Matrix

The matrix described here is implanted using standard surgical techniques for repair or replacement of bone. The matrix can be directly implanted into the site where bone growth is desired, or seeded with appropriate cells such as osteoblasts or osteoblast-like cells and then implanted. In the preferred embodiment, the matrix will be pre-cast into a desired shape for repair of the bone in need of treatment thereof.

Manipulation of Cell Growth Rate

Selection of the polymer side chains can be used to manipulate the rate of cell growth. Although the cells appear to attach equally well to polymers having different side chains, the side chain composition affects the rate of cell growth. In the case of side chains formed of glucosyl, glycinyl or glyceryl units, the growth rate is enhanced relative to growth on other polymers or polyphosphazenes having side chains of predominantly amino acid units such as imidazole.

The present invention will be further understood by reference to the following non-limiting examples.

EXAMPLES 1

Synthesis of poly[(ethyl glycinate)(methylphenoxy) phosphazene]

Polymer Synthesis and Characterization.

Reagents.

All reactions were carried out under an atmosphere of dry nitrogen (Matheson) using standard Schlenk line techniques. Tetrahydrofuran (THF) was dried by distillation from sodium benzophenone ketal under a dry nitrogen atmosphere. Heptane and hexane (Omnisolv) were dried over $MgSO_4$ prior to use. Triethylamine (Fisher) and toluene (Omnisolv) were distilled from $CaH_2$ under a nitrogen atmosphere. p-Methylphenol and imidazole (Aldrich) were sublimed and stored under vacuum prior to use. Ethyl glycinate-HCL (Sigma) and sodium (Aldrich) were used as received. Hexachlorocyclotriphosphazene (Ethyl Corp.) was obtained from a trimer-tetramer mixture by two sublimations (30° C./0.2 mm Hg). Poly(dichlorophosphazene) was prepared as described in Laurencin, et al., *J. Biomater. Res.* 27, 963–973 (1993).

Equipment.

All reactions were monitored by $^{31}$p NMR (36.23 MHz) with the use of a JOEL FX-90Q spectrometer. All $^{31}$p NMR (145 MHz) and $^1$H NMR (360 MHz) of isolated polymers were obtained with the use of a Bruker 360 MHz spectrometer. $^{31}$p NMR chemical shifts are reported in ppm relative to 85% $H_3PO_4$ at 0 ppm. Glass transition temperatures were obtained with a Perkin-Elmer DSC-7 with TAS-7 software. The molecular weight of the polymer was estimated by gel permeation chromatography using a Hewlett Packard HP 1090 Liquid Chromatograph with a polystyrene stationary phase. Sample concentrations were approximately 1.5% (w/v) in THF. Elemental analyses were obtained from Galbraith Laboratories, Knoxville, Tenn.

Synthesis of Poly[(ethyl Glycinato)(methylphenoxy) phosphazenes]

Poly(dichlorophosphazene) (3.0 g, 0.027 mol) was dissolved in dry THF (200 mL). p-Methylphenol (4.2 g, 0.039 mol) is reacted with sodium (0.6 g, 0.026 mol) in dry THF (100 Ml). After the salt had formed, it was added slowly to the polymer solution. The reaction mixture was then brought to reflux for 48 h. Ethyl glycinate-HCl (11.25 g, 0.0807 mol) was suspended in toluene (100 Ml) and triethylamine (11.3 Ml, 0.0807 mol). This mixture was brought to reflux for 4 h. The toluene solution and the polymer solution were then cooled. The triethylamine hydrogen chloride salts were filtered, and the ethyl glycinate solution was added to the partially substituted polymer. This reaction proceeded at room temperature for 10 h. The reaction mixture was then concentrated under vacuum and isolated by precipitation into heptane (5X). The polymer was then dried under vacuum over $P_2O_5$.

Polymer Characterization.

Poly(dichlorophosphazene) was reacted with sodium p-methyl phenoxide to obtain a 50% substituted moiety. The remaining phosphorous-chlorine bonds were replaced by ethyl glycinato to yield a fully substituted poly[(ethyl glycinato) (methyl phenoxy) phosphazene]polymer. The polymer is elastomeric with a glass transition temperature (Tg) of −7.0° C., and a high molecular weight of the order of 1.8×106 Daltons, as shown in Table 1.

TABLE 1

Characterization Data for Poly[(ethyl glycinato) (p-methyl phenoxy) phosphazene]

| | Elemental Analysis | | | |
|---|---|---|---|---|
| | % C | % H | % N | % Cl |
| c. | 49.04 | 5.99 | 12.19 | — |
| f. | 49.19 | 6.02 | 12.12 | 0.26 |

| $^{31}$P NMR | Mw | Tg |
|---|---|---|
| 0.0 | 1.8 × 10⁶ | −7.0 |
| −5.3 | | |
| −18.4 | | | c. = calculated; f. = found.

EXAMPLE 2

Preparation of Porous Three Dimensional Matrix formed of Poly[(ethylglycinato)(methylphenoxy) phosphazene]

One gram of polymer was dissolved in 6 ml of THF and then 4.5 gm of sodium chloride (Aldrich) with a pore size of 150 to 250 μm was added to the dissolved solution. The mixture was then vortexed until the salt was completely dispersed throughout the solution and cast into a 60 mm petri dish (Falcon) lined with Teflon™ coated paper (Bytac, Fisher Scientific, Pittsburgh, Pa.). The film was left at room temperature for 24 h and then freeze dried (Lyph-Lock™ 12, Labconco Corp, Kansas, Mo.) for 12 h to removed traces of THF. The polymer was then placed in three liters of distilled water and the water was replaced frequently. The sample was then freeze dried for 96 hr and placed in 20° C. under Argon until further use.

EXAMPLE 3

Preparation of Non Porous Discs for Cell Growth

One gram of polymer was dissolved in THF to make a 20% w/v solution and cast in a 60 mm petri dish (Falcon) lined with Teflon™ coated paper (Bytac™, Fisher Scientific, Pittsburgh, Pa.). The polymeric material was left for 24 h at room temperature and then freeze dried (Lyph-Lock 12, Labconco Corp, Kansas City, Mo.) for 48 h.

Circular discs 14 mm in diameter were formed using a cork borer. All discs were exposed to ultraviolet light for 10 min on each side, in an effort to minimize contamination.

EXAMPLE 4

Characterization of Polyphosphazene Matrices formed in Examples 2 and 3

The porous and non-porous polymers systems were analyzed using an environmental scanning electron microscopy (ESEM) (Electro Company, Boston, Mass.) with a Trecor Detector. The uncoated samples were set at 5.4 m torr and the experiment was carried out at an accelerating voltage of 30 kv.

The average pore distribution and surface area of the porous discs were measured using mercury intrusion porosity (Model Poresizer 9320, Micronetrics, Norcross, Ga.) equipped with a 5 ml bulb volume (Model 920-61707-00). The filling pressure of the penetrometer was 0.7 psi and the total intrusion volume reached a plateau at a maximum pressure of 30 psi.

Electron micrographs of porous and non-porous poly (organophosphazene) matrices show that the non-porous two poly(organophosphazene) surface is a smooth even surface without pores or a porous network and that the porous surface has a highly porous network throughout the polymer with interconnecting channels. The size and diameter of the pores is between 160 and 200 µm. For the three-dimensional discs, the average pore size, measured mercury porosimetry and ESEM analysis was 165±2.56 µm. In addition, the polymeric three-dimensional polymeric matrix was placed in culture media for 21 days and was found to maintain its porous matrix and interconnected network.

EXAMPLE 5

Cell Culture on Matrices

Cells

Osteoclast-like cells, MC3T3-E1 cells (a gift of Dr. H. Sudo, Tohoku Dental University, Tomitamachi, Koriyma, Japan), were grown in alpha modified Eagles minimal essential media (ICN, Irvine, Calif.) supplemented with 10% fetal bovine serum (Gibco, Grand Island, N.Y.) and 60 mg/ml of kanamycin sulfate (Gibco, Grand Island, N.Y.). The cells were maintained at 37° C. in a fully humidified atmosphere at 5% $CO_2$ in air. The cells were fed every 3 days. After 5 days in culture, the cells were passaged with 0.25 w/v trypsin (Type XI, Sigma Chemical Co., St. Louis, Mo.) in $Ca^{++}$ and $Mg^{++}$ free Tyrode's solution before plating onto the polymer discs.

Cell seeding

Tissue culture plates (24 well, Falcon) were coated with 12% poly(hydroxyethylmethacrylate) (Polysciences, Warrington, Pa.), to ensure that the MC3T3-E1 cells would grow only on the polymer discs contained in the wells and not on the tissue culture polystyrene surface (TCPS). The discs were incubated in 2 ml of media. The cells were plated on the polymer discs at a plating density of $1 \times 10^5$ per $cm^2$ and the media was changed every 24 h.

Cell proliferation was determined at 1, 3, 7, 14 and 21 days by counting total cell population using a hemocytometer. At the predetermined times, the discs were gently washed with phosphate buffered saline (PBS) to remove any unattached cells. The adherent cells were removed from the substrate by incubation in 1 ml of 0.25 w/v trypsin (Type XI) in $Ca^{++}$ and $Mg^{++}$ free Tyrode's solution for 5 min and then discs were washed with 2 ml of media. Cells in the trypsin solution and the media were centrifuged together and then resuspended in fresh media. An aliquot of the resulting cell suspension was counted with a hemocytometer (Fisher Scientific, Pittsburgh, Pa.).

Cell Characterization.

For visualization, cells were stained with 1% w/v cresyl violet acetate (Sigma Chemical Co., St. Louis, Mo.) in 0.1 M acetic acid and photographed using a light microscope (Zeiss Axiophot) after 2 days in culture. For ESEM, the samples were prepared by freeze drying overnight.

Synthesis of the enzyme alkaline phosphatase (ALP) was used as a marker for retention of osteoblast phenotype for cells cultured on porous and nonporous matrices and the control TCPS, after 3, 7 and 14 days in culture, using a commercial diagnostic staining kit (Sigma Chemical Co., St. Louis, Mo., catalog No. 86-R).

Cell Attachment and Growth.

The adhesion and proliferation of MC3T3-E1 cells on two-dimensional and three-dimensional polymers were examined after 1, 3, 7, 14 and 21 days in culture as shown in FIG. 3. On day 1 cell adhesion and proliferation in all poly(organophosphazene) surfaces were comparable to the control (TCPS). By day 3 and 7 there was a significant increase on two-dimensional polymeric surface as compared to TCPS and three-dimensional polymeric systems. Cell growth on two-dimensional polymeric system on day 7 was comparable to TCPS and significantly higher than three-dimensional polymeric system (p<0.01). On day 14, cell growth continued to increase on the three-dimensional polymeric and TCPS surfaces, in contrast to the number of MC3T3-E1 cells counted on the two-dimensional polymeric surface which diminished appreciably during the remaining days of the experiment. By 21 days cell growth was greatest on the TCPS surface, followed by three-dimensional polymeric and two-dimensional polymeric matrix. In general, cell attachment was greatest on two-dimensional polymeric matrix up to day 7, and by day 14 MC3T3-E1 cell growth was found to increase on both the control and three-dimensional polymeric surfaces and remained markedly higher than cells seeded onto the two dimensional matrix.

Cell Morphology (Light Microscopy).

Light microscopy demonstrated that MC3T3-E1 cells with characteristic spindle-like morphology adhered to two-dimensional systems over 21 days. At day 1 cells were found adhered to the three-dimensional polymeric on the surface and a small amount within the matrix. By day 3, MC3T3-E1 cells were proliferated within the matrix and had started to form a monolayer within and on the surface of the polymer. On day 7, the cells spread was homogeneous throughout the polymer. By day 14 and 21, the cells had completely covered the polymer, and confluent within the matrix forming a three-dimensional osteoblast composite. In general, cells were found to proliferate within the matrix as well as on the surface, and by day 21 the pores of the three dimensional matrix were completely populated with adherent and proliferating cells.

MC3T3-E1 cells cultured on poly(organophosphazene) surfaces were tested for retention of their osteoblast-like phenotype by staining for the presence of alkaline phosphatase. Of the stained cells grown on the surfaces, 95% of the cells retained the presence of alkaline phosphatase production, indicating that MC3T3-E1 cells retained their osteoblastic phenotype characteristics in culture on the poly (organophosphazene) matrices.

These studies of osteoblast-like cell growth on two-dimensional erodible systems have shown that poly (organophosphazene) materials are suitable for the construction of a cell-polymer matrix for skeletal tissue regeneration. In order to maximize cell growth in an attempt to establish a complete bone-polymer composite, cells must be able to not only grow on the surface of the polymer, but inside the implant as well. These demonstrate that the porous matrix formed of poly(organophosphazene) having a pore size of between approximately 100 and 250 microns meets these requirements. The pores allow for sufficient space to promote cell fixation and growth, and transport of nutrients for growth maintenance of an intracellular environment. The introduction of porous systems have been shown to increase cell attachment and accumulation around implants. The presence of such pores allows a greater surface area which offers several advantages: (1) better fixation of the biomaterial with the host tissue as a result of tissue ingrowth, (2) possible reduction of inflammation, (3) increase in the rate at which the polymer is absorbed and degrades over time, and (4) channels for the transport of nutrients to cell inside the pores.

Modifications and variations of the present invention will be obvious to those skilled in the art from the foregoing detailed description. Such modifications and variations are intended to come within the scope of the appended claims.

We claim:

1. A polymeric matrix for repair or replacement of bone formed of a biodegradable, biocompatible polyphosphazene formed from the repeat unit

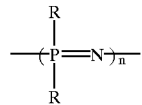

, wherein R is a side chain selected from the group consisting of aliphatic, aryl, aralkyl, alkaryl, carboxylic acid, heteroaromatic, carbohydrates, heteroalkyl, halogen, (aliphatic)amino, heteroaralkyl, di(aliphatic)amino, arylamino, diarylamino, alkylarylamino, oxyaryl, oxyaliphatic, oxyalkaryl, oxyaralkyl, thioaryl, thioaliphatic, NHC(O)O-(aryl or aliphatic), —O—[(CH$_2$)$_x$O]$_y$—(CH$_2$)$_x$NH$_2$, —O—[(CH$_2$)$_x$O]$_y$CH$_2$)$_x$NH(CH2)$_x$SO$_3$H, and —O—[(CH$_2$)$_x$O]$_y$-(aryl or aliphatic), wherein x is 1–8 and y is an integer of 1 to 20, wherein the matrix is a porous structure with pore dimensions of between 100 and 250 microns.

2. The polymeric matrix of claim 1 wherein between 10 and 90% of the side chains on the polyphosphazene are selected from the group consisting of glycine, glycoside, glyceryl, imidazolyl and ethoxy units.

3. The polymeric matrix of claim 1 wherein the polyphosphazene degrades in vivo over a period of between approximately one month and three months.

4. The polymeric matrix of claim 1 further comprising osteoblasts.

5. A method for repair or replacement of bone comprising implanting at a site in need or repair or replacement a polymeric matrix formed of a biodegradable, biocompatible polyphosphazene formed from the repeat unit

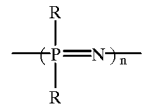

, wherein R is a side chain selected from the group consisting of aliphatic, aryl, aralkyl, alkaryl, carboxylic acid, heteroaromatic, carbohydrates, heteroalkyl, halogen, (aliphatic)amino, heteroaralkyl, di(aliphatic)amino, arylamino, diarylamino, alkylarylamino, oxyaryl, oxyaliphatic, oxyalkaryl, oxyaralkyl, thioaryl, thioaliphatic, NHC(O)O-(aryl or aliphatic), —O—[(CH$_2$)$_x$O]$_y$—CH$_2$)$_x$NH$_2$, —O—[(CH$_2$)$_x$O]$_y$CH$_2$)$_x$NH(CH$_2$)$_x$SO$_3$H, and —O—[(CH$_2$)$_x$O]$_y$-(aryl or aliphatic), wherein x is 1–8 and y is an integer of 1 to 20, wherein the matrix is a porous structure with pore dimensions of between 100 and 250 microns.

6. The method of claim 5 wherein between 10 and 90% of the side chains on the polyphosphazene are selected from the group consisting of glycine, glycoside, glyceryl, imidazolyl and ethoxy units.

7. The method of claim 5 wherein the polyphosphazene degrades in vivo over a period of between approximately one month and three months.

8. The method of claim 1 further comprising seeding the matrix with osteoblasts prior to implantation.

* * * * *